US012285351B2

(12) United States Patent
Nolan et al.

(10) Patent No.: US 12,285,351 B2
(45) Date of Patent: Apr. 29, 2025

(54) OSTOMY APPLIANCE HAVING CONDUCTIVE INK CIRCUIT FOR LEAKAGE DETECTION (71) Applicant: Hollister Incorporated, Libertyville, IL (US)

(72) Inventors: Michael P. Nolan, Chicago, IL (US); Christina Augustyn, Chicago, IL (US); James Brandon Barker, Antioch, IL (US); Jonas P. Carlsson, Chicago, IL (US); Ryan S. Park, Northbrook, IL (US); Scott Janis, El Cerrito, CA (US); Stephanie Henze, San Mateo, CA (US); Christopher Michael Wlezien, Evanston, IL (US); Somasunder Vijay Sekaran, San Francisco, CA (US); Germain Verbrackel, San Francisco, CA (US); Robert Lane, Larkspur, CA (US)

(73) Assignee: HOLLISTER INCORPORATED, Libertyville, IL (US)

( * ) Notice: Subject to any disclaimer, the term of this patent is extended or adjusted under 35 U.S.C. 154(b) by 796 days.

(21) Appl. No.: 17/281,142

(22) PCT Filed: Oct. 3, 2019

(86) PCT No.: PCT/US2019/054484
§ 371 (c)(1),
(2) Date: Mar. 29, 2021

(87) PCT Pub. No.: WO2020/076607
PCT Pub. Date: Apr. 16, 2020

(65) Prior Publication Data
US 2021/0338471 A1   Nov. 4, 2021

Related U.S. Application Data (60) Provisional application No. 62/743,233, filed on Oct. 9, 2018.

(51) Int. Cl.
*A61F 5/44* (2006.01)
*A61F 5/443* (2006.01)
(Continued)

(52) U.S. Cl.
CPC ............ *A61F 5/4404* (2013.01); *A61F 5/443* (2013.01); *A61F 5/448* (2013.01); *G01M 3/16* (2013.01)

(58) Field of Classification Search
CPC ........ A61F 5/4404; A61F 5/443; A61F 5/448; A61F 5/445; A61F 13/42;
(Continued)

(56) References Cited

U.S. PATENT DOCUMENTS 4,775,374 A * 10/1988 Cilento ............. B29C 66/24221
604/338
9,216,104 B2   12/2015 Thirstrup et al.
(Continued)

FOREIGN PATENT DOCUMENTS

GB        2431239 A      4/2007
WO     2007098762 A1    9/2007
(Continued)

OTHER PUBLICATIONS

International Search Report issued by ISA/EPO in connection with PCT/US2019/054484 on Mar. 19, 2020.
(Continued)

*Primary Examiner* — Philip R Wiest
*Assistant Examiner* — Brandon W. Levy
(74) *Attorney, Agent, or Firm* — Klintworth & Rozenblat IP LLP (57) ABSTRACT An ostomy appliance includes a substrate and at least one Radio Frequency Identification (RFID) circuit disposed on the substrate. The RFID circuit includes a RFID transponder having an antenna and a conductive ink connected in series
(Continued)

with the antenna and the RFID transponder. The conductive ink is configured to dissolve in response to exposure to moisture. The RFID circuit is in a closed condition when the conductive ink extends continuously between the RFID transponder and the antenna. The RFID circuit is in an open condition when at least a portion of the conductive ink is dissolved.

11 Claims, 10 Drawing Sheets

(51) Int. Cl.
*A61F 5/448* (2006.01)
*G01M 3/16* (2006.01)

(58) Field of Classification Search
CPC ............ A61F 13/00051; A61F 13/0246; A61F 2013/424; G01M 3/16; G01N 27/223; G16H 40/67; A61B 5/746
See application file for complete search history.

(56) References Cited

U.S. PATENT DOCUMENTS

| | | | |
|---|---|---|---|
| 9,782,302 B2 | 10/2017 | Johnson et al. | |
| 2004/0100376 A1* | 5/2004 | Lye | A61B 5/411 600/300 |
| 2005/0236603 A1* | 10/2005 | Faris | C09D 11/52 252/500 |
| 2006/0226008 A1* | 10/2006 | Rodgers | C09D 11/106 204/403.14 |
| 2010/0030167 A1 | 2/2010 | Thirstrup et al. | |
| 2014/0051946 A1 | 2/2014 | Arne et al. | |
| 2014/0249760 A1* | 9/2014 | Proud | A61B 5/443 702/19 |
| 2017/0079576 A1* | 3/2017 | Stroebech | A61B 5/445 |
| 2017/0140103 A1 | 5/2017 | Angelides | |
| 2019/0142623 A1 | 5/2019 | Norman et al. | |
| 2019/0240059 A1 | 8/2019 | Michael et al. | |
| 2020/0000624 A1* | 1/2020 | Gibbons | A61B 5/444 |
| 2020/0246174 A1 | 8/2020 | Ask et al. | |
| 2020/0246175 A1 | 8/2020 | Ask et al. | |
| 2020/0246176 A1 | 8/2020 | Ask et al. | |
| 2020/0246177 A1 | 8/2020 | Ask et al. | |
| 2021/0275341 A1 | 9/2021 | Kristoffer | |
| 2021/0353448 A1 | 11/2021 | George et al. | |
| 2021/0369491 A1 | 12/2021 | Holden | |
| 2022/0117771 A1 | 4/2022 | Fearn et al. | |
| 2022/0257405 A1 | 8/2022 | Peder et al. | |
| 2022/0265457 A1 | 8/2022 | Jonas et al. | |
| 2022/0313473 A1 | 10/2022 | Olav et al. | |
| 2023/0031979 A1 | 2/2023 | Stendevad et al. | |

FOREIGN PATENT DOCUMENTS

| | | |
|---|---|---|
| WO | 2017023794 A1 | 2/2017 |
| WO | 2018028756 A1 | 2/2018 |
| WO | 2019/094635 A1 | 5/2019 |
| WO | 2019/120424 A1 | 6/2019 |
| WO | 2019/120425 A1 | 6/2019 |
| WO | 2019/120426 A1 | 6/2019 |
| WO | 2019/120427 A1 | 6/2019 |
| WO | 2019/120428 A1 | 6/2019 |
| WO | 2019/120429 A1 | 6/2019 |
| WO | 2019/120430 A1 | 6/2019 |
| WO | 2019/120432 A1 | 6/2019 |
| WO | 2019/120433 A1 | 6/2019 |
| WO | 2019/120434 A1 | 6/2019 |
| WO | 2019/120435 A1 | 6/2019 |
| WO | 2019/120436 A1 | 6/2019 |
| WO | 2019/120437 A1 | 6/2019 |
| WO | 2019/120440 A1 | 6/2019 |
| WO | 2019/120441 A1 | 6/2019 |
| WO | 2019/120442 A1 | 6/2019 |
| WO | 2019/120443 A1 | 6/2019 |
| WO | 2019/120444 A1 | 6/2019 |
| WO | 2019/120445 A1 | 6/2019 |
| WO | 2019/120446 A1 | 6/2019 |
| WO | 2019/120448 A1 | 6/2019 |
| WO | 2019/120449 A1 | 6/2019 |
| WO | 2019/120450 A1 | 6/2019 |
| WO | 2019/120451 A1 | 6/2019 |
| WO | 2019/120452 A1 | 6/2019 |
| WO | 2019/120453 A1 | 6/2019 |
| WO | 2019/120458 A1 | 6/2019 |
| WO | 2019/149330 A1 | 8/2019 |
| WO | 2019/161859 A1 | 8/2019 |
| WO | 2019/161860 A1 | 8/2019 |
| WO | 2019/161861 A1 | 8/2019 |
| WO | 2019/161862 A1 | 8/2019 |
| WO | 2019/161863 A1 | 8/2019 |
| WO | 2019/174687 A1 | 9/2019 |
| WO | 2019/174692 A1 | 9/2019 |
| WO | 2019/174693 A1 | 9/2019 |
| WO | 2019/174694 A1 | 9/2019 |
| WO | 2019/174695 A1 | 9/2019 |
| WO | 2019/174696 A1 | 9/2019 |
| WO | 2019/174697 A1 | 9/2019 |
| WO | 2019/174698 A1 | 9/2019 |
| WO | 2019/174699 A1 | 9/2019 |
| WO | 2019/238180 A1 | 12/2019 |
| WO | 2019/238181 A1 | 12/2019 |
| WO | 2019/238182 A1 | 12/2019 |
| WO | 2019/238183 A1 | 12/2019 |
| WO | 2020/035121 A1 | 2/2020 |
| WO | 2020/123771 A2 | 6/2020 |
| WO | 2020/156624 A1 | 8/2020 |
| WO | 2020/156625 A1 | 8/2020 |
| WO | 2020/156626 A1 | 8/2020 |
| WO | 2020/169162 A1 | 8/2020 |
| WO | 2020/173534 A1 | 9/2020 |
| WO | 2020/216426 A1 | 10/2020 |
| WO | 2020/216427 A1 | 10/2020 |
| WO | 2020/216429 A1 | 10/2020 |
| WO | 2020/259775 A1 | 12/2020 |
| WO | 2021/063463 A1 | 4/2021 |
| WO | 2021/063466 A1 | 4/2021 |
| WO | 2021/165703 A1 | 8/2021 |
| WO | 2021/165705 A1 | 8/2021 |
| WO | 2021/185425 A1 | 9/2021 |
| WO | 2021/209104 A1 | 10/2021 |
| WO | 2022/063379 A1 | 3/2022 |
| WO | 2022/078561 A1 | 4/2022 |
| WO | 2022/207049 A1 | 10/2022 |

OTHER PUBLICATIONS

Written Opinion issued by ISA/EPO in connection with PCT/US2019/054484 on Mar. 19, 2020.
International Preliminary Report on Patentability issued by ISA/EPO in connection with PCT/US2019/054484 on Apr. 8, 2021.
European Extended Search Report for EP Application No. 24152610.2, dated May 10, 2024, 7 pages.

* cited by examiner

OSTOMY APPLIANCE HAVING CONDUCTIVE INK CIRCUIT FOR LEAKAGE DETECTION

This is a National Stage Application of International Patent Application No. PCT/US2019/054484, filed Oct. 3, 2019, which claims the benefit of and priority to U.S. Provisional Application No. 62/743,233 filed Oct. 9, 2018, the entirety of which are incorporated fully herein by reference.

BACKGROUND

The following description relates generally to an ostomy appliance having a conductive ink circuit for detecting leakage.

An ostomy pouch includes opposing sidewalls defining an internal collection area. One of the sidewalls is provided with an inlet opening to receive a stoma, and means to secure the pouch to the user. Such means include, for example, an ostomy barrier, faceplate or skin barrier ring which may be connected to or formed integrally with the sidewall having the inlet opening. The ostomy barrier (or faceplate or barrier ring) may include adhesive on a skin-facing side to seal against the user's skin in an area surrounding the stoma. Such a system is intended to prevent or limit leakage of bodily fluid discharged from the stoma through the stoma/barrier/pouch environment.

However, the seal formed between the ostomy barrier and the user may weaken, for example, with time, movement, improper installation and/or application of an external force, and thus, become susceptible to leaking. Often times, the user is unaware of or cannot easily assess an extent of weakening in the seal. Thus, a user is typically not aware of a weakened seal, and consequently, the risk of leakage, until a fluid discharged from the stoma leaks through to an exterior of the seal (i.e., the barrier) and becomes undesirably exposed to an external environment outside of the stoma/barrier/pouch environment.

Efforts have been made in the art to detect leakage of fluid before the fluid escapes to the exterior environment. For example, WO 2018/028756 ("WO '756") discloses an ostomy appliance having a signal generator adapted to give a user or a health care professional a warning in time to change the appliance before leakage occurs by predetermining leakage or potential leakage of stomal fluids. In WO'756, a second material may be configured to dissipate in response to being exposed to stomal fluids and a signal generator, generally disposed under or within the second material, may set off an indicator signal when dissipation of the second material reaches a pre-defined threshold value.

In US Pat. Appl. Pub. No. 2017/0140103 ("US '103"), a parameter sensor that uses ink jet electrodes printed on paper can be used to measure leakage. The sensor paper is placed at a site of ostomy bag attachment to the stoma with the sensor paper surrounding the stoma. As the paper gets wet, from leakage, the electrodes change resistance and report this to a communicator.

Another system for detecting leakage is described in U.S. Pat. No. 9,216,104 ("US '104"). In US '104, a dressing is provided for application to an object that is, at least partly, electrically conductive. The dressing includes at least two electrodes adapted to be arranged at a distance from the partly electrically conductive object so that a first capacitor is formed between the first electrode and the partly electrically conductive object, and a second capacitor is formed between a second electrode and the partly electrically conductive object.

However, the systems above may still require frequent visual or manual monitoring, may be undesirably complex, or may not be suitably accurate.

Other systems have been proposed for sensing wetness, for example, as described in U.S. Pat. No. 9,782,302 ("US '302"). In US '302, a wetness sensor includes a substrate that carries a tuned RF circuit. The circuit includes a conductive pattern applied to the substrate, a capacitor, and a jumper disposed on a same side of the substrate. The conductive pattern includes an inductive coil and an inner and outer terminus. The jumper electrically couples the inner terminus to the outer terminus and also includes a frangible link which, when contacted by a target fluid, produces a drastic change in the operation of the RF circuit. The drastic change can be interpreted by a remote reader as a "wet" condition. Contact of the frangible link by the target fluid may change the impedance or resistance of the RF circuit by at least a factor of 5, 10, 100, or more, and/or may cause the frangible link to disintegrate to produce an open circuit, and/or may substantially render the RF circuit inoperative. However, the system of US '302 is part of an absorbent article or garment, such as a diaper, and is not configured for an ostomy environment.

Accordingly, it is desirable to provide an ostomy appliance, such as an ostomy hydrocolloid or ostomy pouch having such an ostomy hydrocolloid, in which leakage may be detected using a conductive ink circuit. It is also desirable to provide an ostomy appliance in which a notification may be provided to the user based on the leakage detection, before the leakage reaches the exterior environment. It is also desirable to provide an ostomy appliance in which an extent of leakage may be detected.

SUMMARY

According to one embodiment, an ostomy appliance includes a substrate and at least one Radio Frequency Identification (RFID) circuit disposed on the substrate. The at least one RFID circuit includes a RFID transponder having an antenna and a conductive ink connected in series with the antenna and the RFID transponder. The conductive ink is a dissolvable ink configured to dissolve in response to exposure to moisture. The RFID circuit is in a closed condition when the conductive ink extends continuously between the RFID transponder and the antenna. The RFID circuit is in an open condition when at least a portion of the conductive ink is dissolved.

The at least one RFID circuit may include a plurality of the RFID circuits. Each RFID circuit of the plurality RFID circuits may have a different transverse dimension than each of the other RFID circuits of the plurality of RFID circuits. The RFID circuits may be concentrically positioned relative to one another. The RFID circuits of the plurality of RFID circuits may extend along respective, substantially circular paths.

The ostomy appliance may further include an ostomy hydrocolloid having a skin barrier, a backing layer and a stoma opening. The at least one RFID circuit may be disposed on the skin barrier. The ostomy appliance may further include an ostomy pouch coupled to the ostomy hydrocolloid.

In one embodiment, the ostomy appliance may further include a wearable device communicatively connected to the at least one RFID circuit. The wearable device may include a housing, a power supply, a controller operably connected to the power supply and an RFID transceiver operably connected to a transceiver antenna and the controller. The RFID transceiver may be configured to transmit a first signal, and the RFID transponder may be configured to transmit a second signal in response receiving the first signal with the RFID circuit in a closed condition. In addition, the RFID may not be configured to transmit the second signal with the RFID circuit in the open condition. The controller may be configured to determine a leakage condition of the ostomy appliance based on the second signal. The wearable device may also include an output device configured to output a notification based on the determined leakage condition of the ostomy appliance. The wearable device may also include a wireless transceiver.

According to one embodiment, the ostomy appliance may further include a personal notification device communicatively connected to the wearable device via a wireless transceiver. The personal notification device may be configured to output a notification based on the determined leakage condition. The personal notification device may be a smartphone.

In an embodiment, an ostomy appliance may comprise a hydrocolloid and a leak detection system. The leakage detections system may comprise at least one ink jet electrode arranged on the hydrocolloid. The at least one ink jet electrode may be configured to reduce a conductivity when exposed to ostomy leakage fluid. The leak detection system may be configured to measure electrical current flowing through the at least one ink jet electrode and detect a leakage by measuring a change in electrical current flowing through the at least one ink jet electrode.

The leak detection system may further include at least one RFID circuit comprising a RFID transponder having an antenna, wherein the at least one ink jet electrode is connected in series with the antenna and the RFID transponder. The RFID circuit may be configured to form a closed circuit with the at least one ink jet electrode extending between the RFID transponder and the antenna. In an embodiment, the at least one ink jet electrode may be formed from a conductive ink that dissolves when exposed to ostomy leakage fluid, wherein the RFID circuit becomes an open condition when at least a portion of the at least one ink jet electrode is dissolved. In another embodiment, the at least one ink jet electrode may be configured to absorb ostomy leakage fluid and swell, wherein the conductivity is reduced when the at least one ink jet electrode absorbs the fluid and swells.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 1:
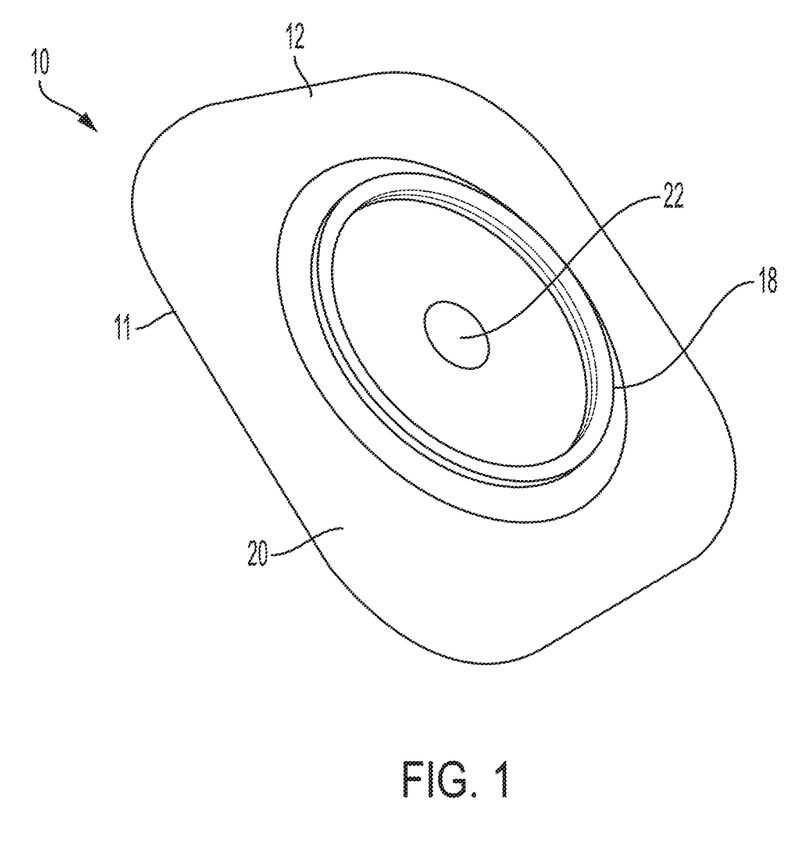
FIG. 1 is a perspective view of an ostomy appliance, according to an embodiment.
Figure 2:
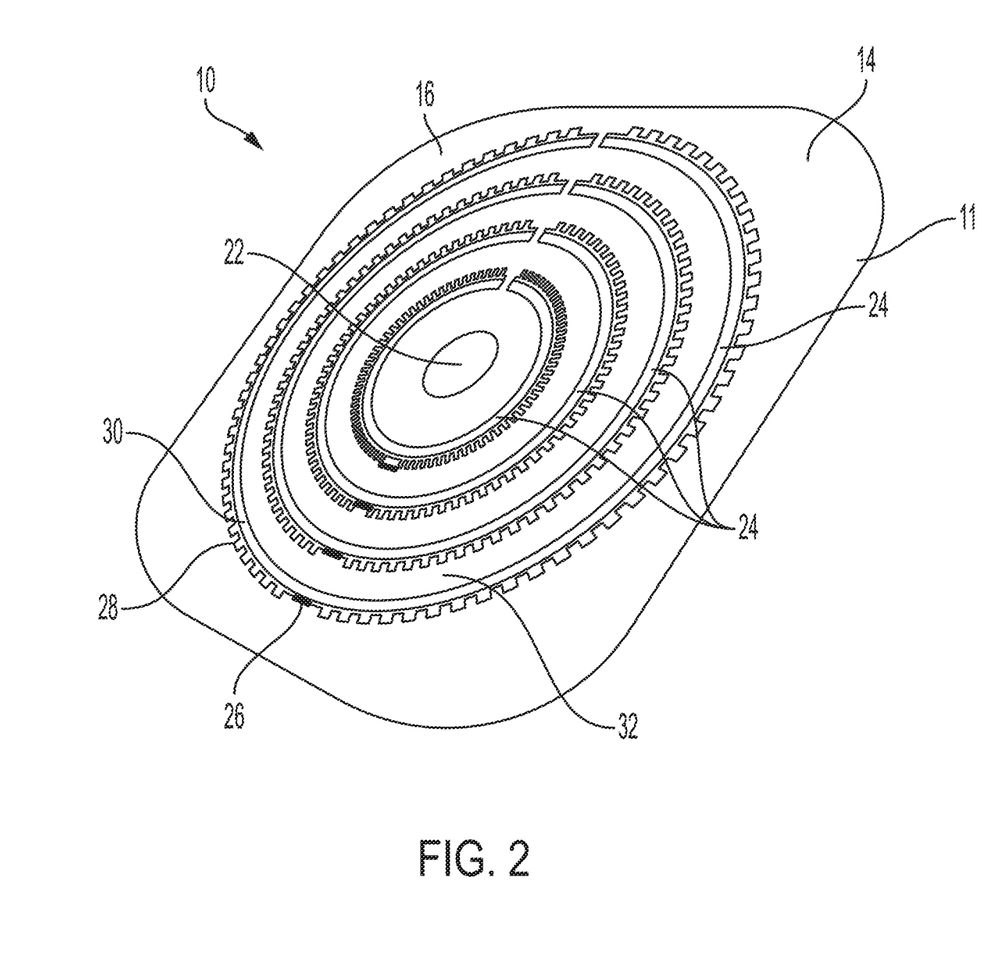
FIG. 2 is another perspective view of the ostomy appliance of FIG. 1.

FIG. 1 is a perspective view showing a pouch-facing side of an ostomy appliance 10, according to an embodiment, and FIG. 2 is another perspective view of the ostomy appliance 10 of FIG. 1, showing a body-facing side of the appliance 10. In one embodiment, the ostomy appliance 10 includes an ostomy hydrocolloid 11 configured to connect an ostomy pouch 210 (FIG. 7) to a user. The ostomy hydrocolloid 11 may be, for example, any of an ostomy barrier, an ostomy faceplate or an ostomy skin barrier ring. In one embodiment, the ostomy hydrocolloid 11 generally includes a backing layer 12 (FIG. 1) and a skin barrier 14 (FIG. 2). The backing layer 12 may be formed by a soft, flexible material that is generally soft and non-irritable to the user's skin, such as a nonwoven or foam material. In one embodiment, an adhesive may be provided on the body-facing side 16 of the ostomy appliance 10 for adhering to the user's skin. The skin barrier 14 may include a known, medical grade adhesive suitable for adhering to the user's skin and sealing around a stoma.

The ostomy appliance 10 may further include a coupling section 18 at the pouch-facing side 20 of the ostomy appliance 10. In one embodiment, the coupling section 18 may be a known ostomy appliance flange configured for coupling to an ostomy pouch in a two-piece pouch configuration. In another embodiment, the coupling section 18 may be a known bag-barrier interface in a one-piece pouch configuration.

The ostomy appliance 10 includes a stoma opening 22 extending through the backing layer 12 and the skin barrier 14. The stoma opening 22 is configured to receive the stoma and allow for flow of stoma fluid into the ostomy pouch.

Figure 3:
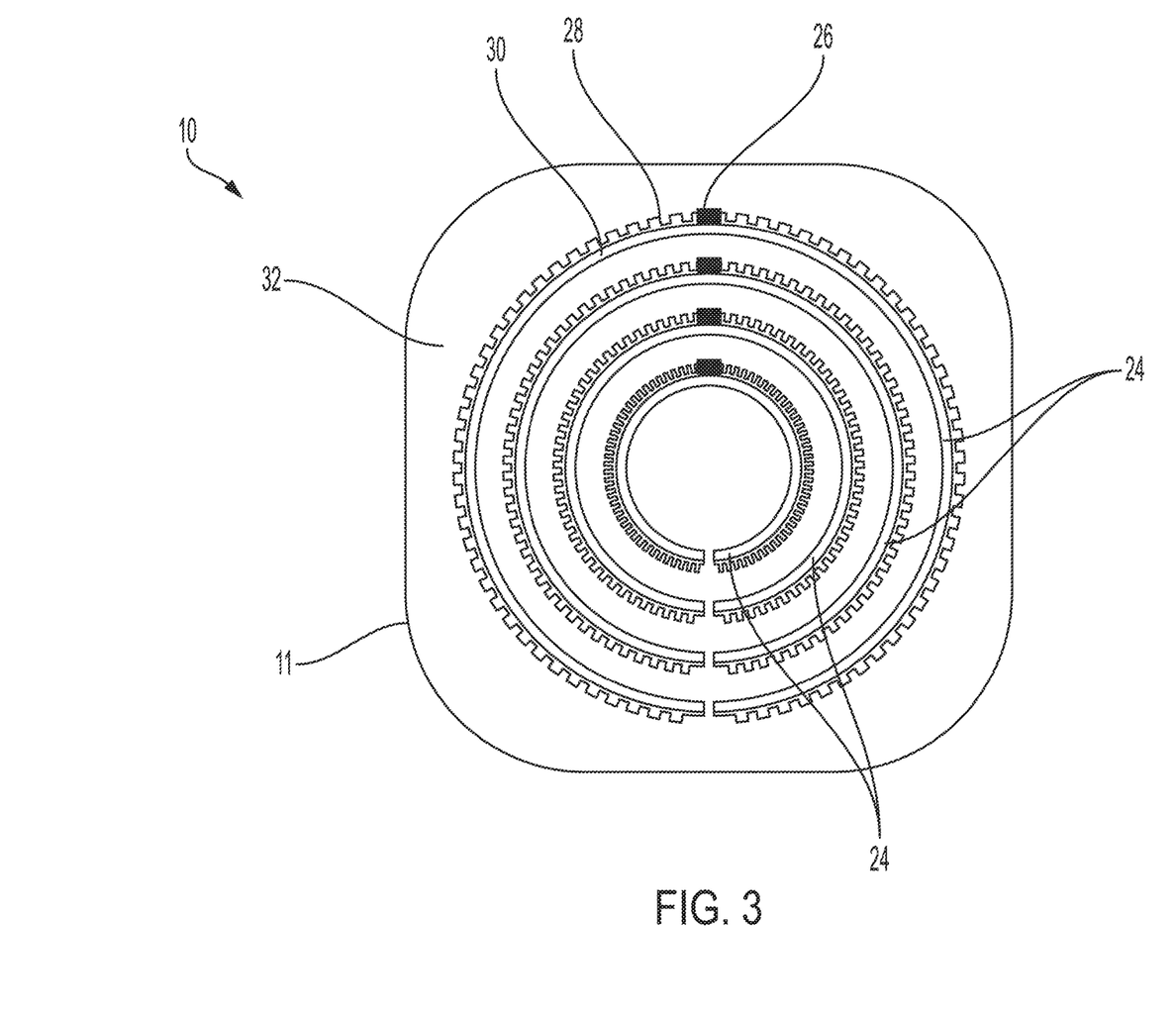
FIG. 3 is a plan view showing a body-facing side of the ostomy appliance of FIG. 2, according to an embodiment.

FIG. 3 is a plan view of the body-facing side 16 of the ostomy appliance 10, according to an embodiment. With reference to FIGS. 2 and 3, a Radio Frequency Identification (RFID) circuit 24 is provided at the skin barrier 14. In one embodiment, the RFID circuit 24 includes a RFID transponder 26 having an antenna 28 and an electrically conductive ink 30 connected in series with the antenna 28 and the RFID transponder 26. In one embodiment, the RFID circuit 24 may also include a suitable device (not shown) for detecting an electrical resistance, for example, by detecting a voltage drop across the circuit. In one embodiment, the RFID circuit 24 includes a plurality of the RFID circuits 24. In one embodiment, the plurality of RFID circuits 24 may include, for example, at least two RFID circuits 24, and up to ten RFID circuits 24. Alternatively, a single RFID circuit 24 may be provided.

In one embodiment, the RFID transponder 26 is configured to operate in accordance with a local standard. For example, in the United States, the RFID transponder 26 may operate in accordance with Ultra-High Frequency, or UHF, RFID technology, which operates at frequency range from 902 MHz to 928 MHz. The present disclosure is not limited to such a frequency range, however.

The conductive ink 30 may be configured to degrade and/or change a property when exposed to moisture. For example, the conductive ink 30 may be configured to absorb moisture and/or fluid and swell and become non-conductive. In an embodiment, the conductive ink 30 may be dissolvable when exposed to moisture. The conductive ink 30 portions of the RFID circuit 24 may also be referred to as "ink jet electrodes" herein. In one embodiment, the conductive ink 30 may be carbon-based, such as a carbon-based conductive ink 30 sold by BARE CONDUCTIVE. However, other electrically conductive inks are envisioned for use in the RFID circuit 24 as well. The RFID circuit 24 is in a closed condition when the conductive ink 30 extends continuously between the RFID transponder 26 and the antenna 28, such that an electrical current may flow through the circuit 24. The RFID circuit 24 is in an open condition when at least a portion of the conductive ink 30 is dissolved, thereby preventing or limiting flow of an electrical current in the circuit.

The RFID circuit 24 may be formed on a substrate 32 for example, by printing. In one embodiment, the substrate 32 may be a release paper (FIG. 3) configured to be applied over the body-facing side 16 of the ostomy appliance 10 to dispose the RFID circuit 24 on the skin barrier 14. Accordingly, the RFID circuit 24 may be manufactured independently from the ostomy hydrocolloid 11 and provided separately as an accessory for use with the ostomy hydrocolloid 11. In one embodiment, the substrate 32 may be formed having the stoma opening 22, a stoma opening starter hole, or be configured to have the stoma opening 22 formed therein in a post-manufacturing step, for example, by the user. In another embodiment, the substrate 32 may be the skin barrier 14 of the ostomy hydrocolloid 11 (FIG. 2) such that the RFID circuit 24 is disposed directly on the skin barrier 14.

In one embodiment, each RFID circuit 24 of the plurality of RFID circuits 24 may be formed having a different transverse dimension. For example, each RFID circuit 24 may have a radius different from the other RFID circuits 24. In one embodiment, the RFID circuits 24 may be arranged concentrically relative to one another. Further still, the RFID circuits 24 may be concentric with the stoma opening 22 of the ostomy appliance 10. In one embodiment, the RFID circuits 24 extend along respective substantially circular or curved paths. However, other suitably shaped paths are envisioned as well. In one embodiment, the RFID circuits 24 extend 360 degrees, or substantially 360 degrees, about the stoma opening 22. In another embodiment, the RFID circuits 24 may extend along a path only partially about the stoma opening at a location where leakage is most likely to occur.

Figure 4:
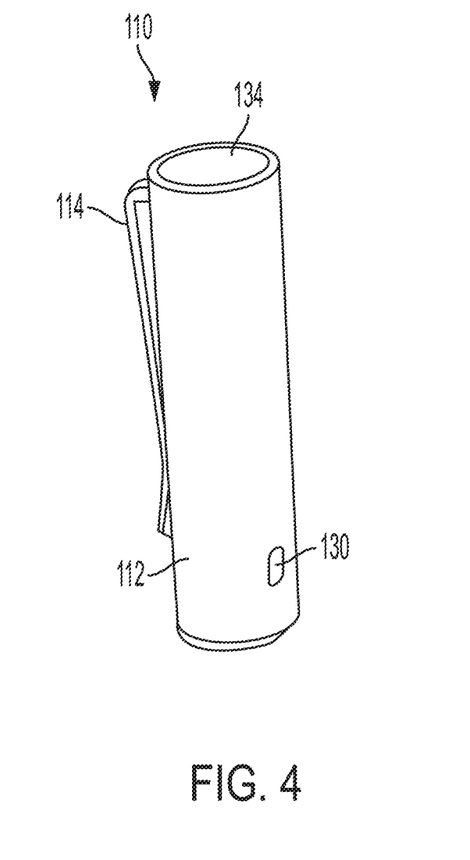
FIG. 4 is a perspective view of a wearable device, according to an embodiment.

FIG. 4 is a perspective view of a wearable device 110 according to an embodiment. In one embodiment, the wearable device 110 includes a housing 112. The housing 112 is preferably made from a relatively lightweight, durable material. The material of the housing 112 is preferably a skin-friendly material as well. The housing 112 may include a fastener 114 configured to secure the wearable device 110 to the user, for example, on an article of clothing or other accessory. Examples of the fastener 114 include, but are not limited to, a clip, a hook-and-loop fastener, a button, a snap, a pin, an adhesive, a strap or other flexible material, a buckle, and the like.

Figure 5:
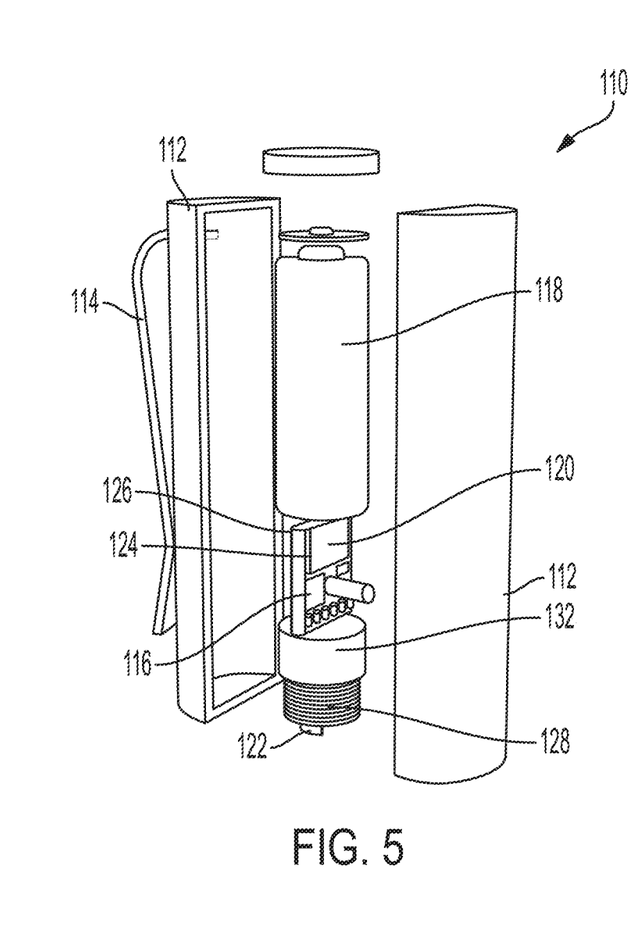
FIG. 5 is an exploded view of the wearable device, according to an embodiment.
Figure 8:
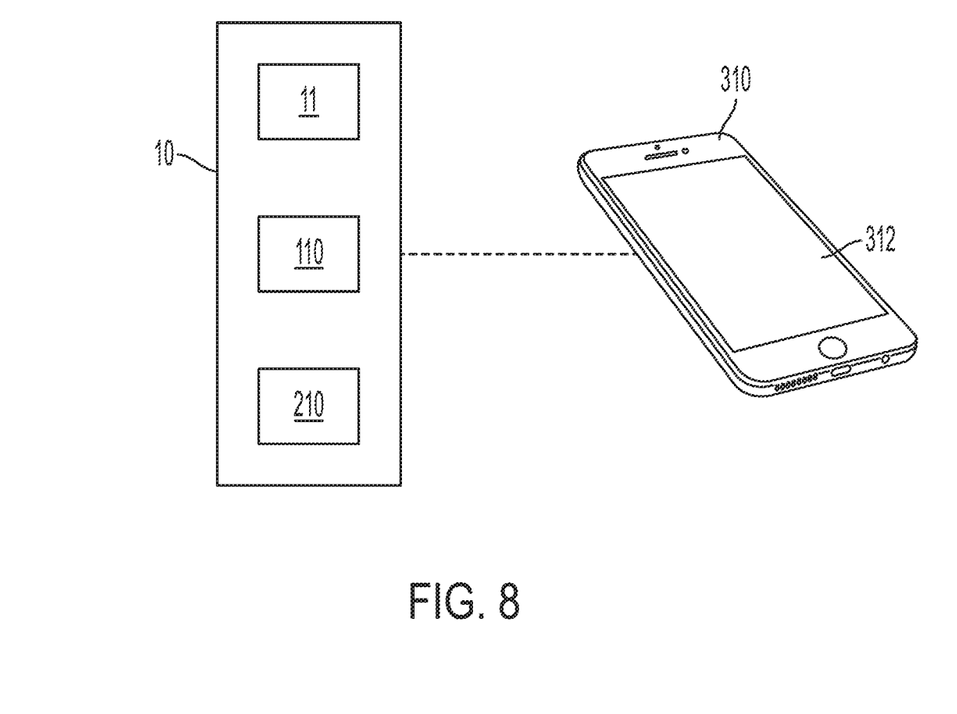
FIG. 8 schematically shows a personal notification device communicatively connected to the ostomy appliance, according to an embodiment.

FIG. 5 is an exploded view of the wearable device 110 according to an embodiment. The wearable device 110 includes, for example, a controller 116, a power supply 118, such as a battery, a RFID transceiver 120 (also referred to as a RFID reader), and a first charging interface 122, such as pogo pins, for facilitating charging the power supply 118. The wearable device 110 may also include a wireless transceiver 124 configured to facilitate wireless communications with a personal notification device 310 (FIG. 8). In one embodiment, the controller 116, power supply 118, RFID transceiver 120 and wireless transceiver 124 may be operably connected to one another. In one embodiment, a printed circuit board (PCB) 126 may also be provided and connected to the various components described above.

The controller 116 may be a microcontroller and may include a processor, memory and communication module. The processor is configured to execute program instructions stored in the memory and the communication module is configured to send or receive signals to and from the processor to carry out operations based on the program instructions.

In one embodiment, the wireless transceiver 124 may be configured for wireless communications according to known wireless communication standards and protocols and may communicate over known communication networks, such as personal area networks, wireless local area networks, metropolitan area networks and wide area networks. Accordingly, the wireless transceiver 124 may be configured for various wireless communications including, but not limited to, Bluetooth, Bluetooth Low Energy, Near-Field Communication, WiFi, WiMax, cellular LTE or other cellular radio communications.

The RFID transceiver 120 is operably connected to a transceiver antenna 128, which may be formed as a coil, to facilitate RFID communications. Accordingly, the RFID transceiver 120 may be configured to transmit a first signal, such as an interrogation signal, and receive a second signal, such as a response signal as further described below.

In one embodiment, the wearable device 110 may further include one or more output devices 130, 132 configured to output a notification. The one or more output devices 130, 132 may include, for example, one or more of a visual indicator such as a light emitting device, an audio indicator such as a speaker, or a vibratory indicator such as a vibrating motor. In one embodiment, the one or more output devices 130, 132 include a light emitting diode (LED) 130 and a vibrating motor 132. However, it is understood that other, additional or fewer output devices, or combinations of output devices, are envisioned as well.

In one embodiment, the wearable device 110 may further include an operating switch 134, which may be formed as pushbutton, sliding switch, rocker switch, haptic switch or other similar, suitable switch or button. The switch 134 may be operably coupled to the power supply 118 and function as an ON/OFF switch for the wearable device 110. In one embodiment, the operating switch 134 may also function to sync or pair the wearable device 110 with the sensor 24 of the ostomy appliance 10 to facilitate communication between the one or more RFID circuits 24 and the wearable device 110. In another embodiment, a separate sync or pair switch may be provided for the syncing or pairing function. In one embodiment, syncing or pairing may occur when the wearable device 110 is powered on and positioned within range of the RFID circuit 24. In one embodiment, the range may be up to about 1 meter. Thus, in one embodiment, the first and second signals may be transmitted between the RFID transponder 26 and the RFID transceiver 120 within a range of up to about 1 meter.

In the embodiments above, the RFID circuit 24 is configured to receive the first signal from the RFID transceiver 120. With the RFID circuit 24 in the closed condition, the receipt of the first signal induces an electrical current through antenna 28 and conductive ink 30 to provide power to the RFID transponder 26. The RFID transponder 26 may transmit the second signal to the RFID transceiver 120. The second signal includes RFID information in the form of analog or digital data. RFID information may include, for example, identification information of the RFID transponder 26 or circuit 24 from which the second signal is transmitted.

The conductive ink 30 may be configured to degrade and/or change a property when exposed to moisture. In an embodiment, the conductive ink 30 is configured to dissolve in response to exposure to moisture. Accordingly, stoma fluid leakage from the stoma opening 22 may contact the conductive ink 30 causing the conductive ink 30 to dissolve. With at least a portion of the conductive ink 30 dissolved, the RFID circuit 24 becomes an open circuit. In the open circuit condition, electrical current may not be provided to the RFID transponder 26, and thus, the second signal may not be transmitted. In some embodiments, the ostomy appliance 10 may be configured to facilitate transport of stoma fluid leakage toward the conductive ink 30 for timely leak detection. For example, the hydrocolloid 11 of the ostomy appliance 10 may be configured to guide and transport stoma fluid leakage toward the conductive ink 30. In another example, the ostomy appliance 10 may include a wick arranged and configured to guide and transport ostomy fluid leakage toward the conductive ink 30.

The RFID transceiver 120 is configured to receive the second signal and the controller 116 is configured to process the second signal to determine a condition of the ostomy appliance 10. The determined condition may indicate that stoma fluid leakage is not detected, that stoma fluid leakage is detected, and in one embodiment, an extent of the detected stoma fluid leakage. The extent of stoma fluid leakage may be either qualitative or quantitative, and may refer to a distance or location relative to a reference point on the ostomy hydrocolloid 11 where stoma fluid leakage has been detected. The reference point may be, for example the stoma opening 22 or an outer periphery of the ostomy hydrocolloid 11.

In one embodiment, the controller 116 may determine that stoma fluid leakage is not detected if the second signal is received from the RFID circuit 24, or each RFID circuit 24 of the plurality of RFID circuits 24, in response to transmission of the first signal.

In one embodiment, the controller 116 may determine that stoma fluid leakage is detected if the second signal is not received from the RFID circuit 24, or the second signal is received from less than all RFID circuits 24 of the plurality of RFID circuits 24, in response to transmission of the first signal.

In one embodiment, the controller 116 may determine an extent of the detected stoma fluid leakage, for example, by determining which RFID circuits 24 of the plurality of RFID have, or have not, transmitted the second signal in response to transmission of the first signal. In one embodiment, a position of the RFID circuits 24 on the ostomy hydrocolloid 11 may be known, such that a quantitative indication of the extent of the stoma fluid leakage may be determined.

In one embodiment, as the conductive ink 30 dissolves, an electrical resistance may be detected in the RFID circuit 24. In one embodiment, the detected electrical resistance may be included as resistance information in the RFID information. The controller 116 may then determine whether or not a stoma fluid leak is present at an RFID circuit 24 based on the resistance information received in the second signal. For example, the controller 116 may determine that a stoma fluid leak is present if the resistance information is transmitted with the second signal. Alternatively, the controller 116 may compare the received resistance information to stored, predetermined threshold resistance information.

In one embodiment, the wearable device 110 is configured to output a notification based on the determined condition of the ostomy appliance 10. For example, the controller 116 may be configured to output the notification by controlling one or more of the output devices 130, 132 based on the determined condition. For example, the controller 116 may control the LED 130 to emit light in one more colors depending on the determined condition. In one embodiment, the LED 130 may emit a green light to indicate that no stoma fluid leakage is detected, a yellow light to indicate that a non-urgent stoma fluid leak is detected which does not require immediate attention, and a red light indicating that a stoma fluid leak is detected at an extent such that the ostomy appliance should be promptly tended to. The "non-urgent" condition of the stoma fluid leak may be determined based on the extent of stoma fluid leak. In one embodiment, the controller 116 may determine a rate of change of a stoma fluid leak, for example, by monitoring which RFID circuits 24 transmit the second signal with respect to time. In one embodiment, the determined condition may be based, at least in part, on the determined rate of change.

The LED 130 could also be controlled, for example, to blink, blink at different frequencies, or emit light at varying intensities, or any combination thereof, based on the determined condition. Alternatively, or in addition, the controller 116 may control the vibrating motor 132, for example, to vibrate, not vibrate, vibrate intermittently, or at different intensities, or any combination thereof, based on the determined condition. Similarly, an audible output device (not shown) may be controlled to emit, for example, a sound, at different time intervals, pitches, volumes, or any combination thereof, based on the determined condition. Notifications including combinations of the above may be output as well.

Figure 6:
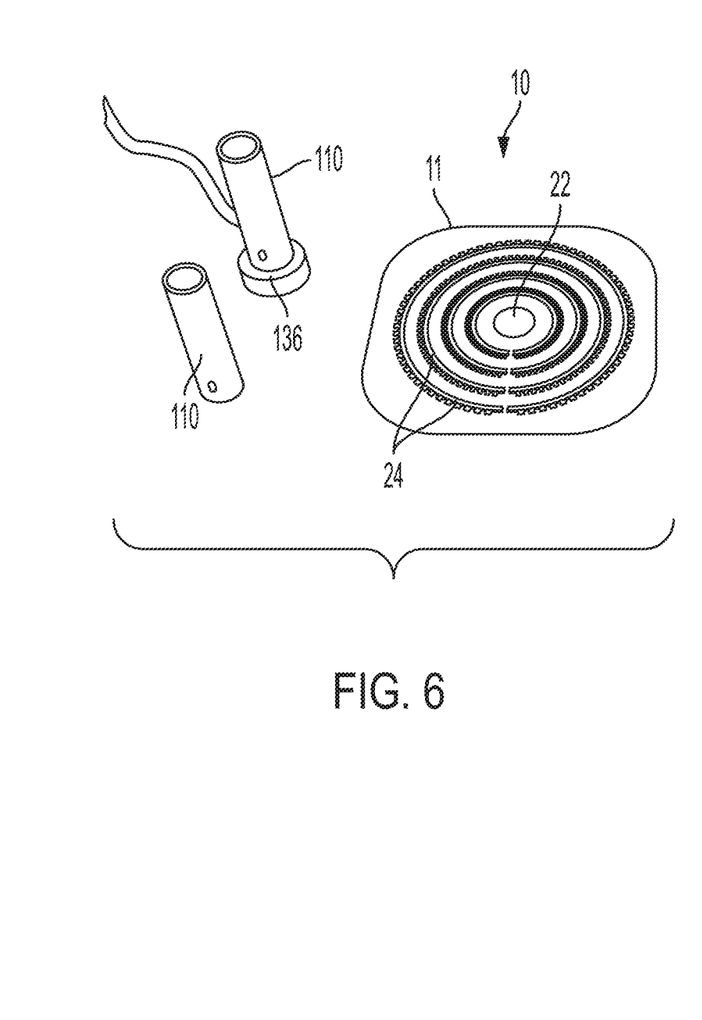
FIG. 6 shows an ostomy hydrocolloid and the wearable device of the ostomy appliance, according to an embodiment.

FIG. 6 shows examples of the ostomy hydrocolloid 11 and the wearable device 110 of the ostomy appliance 10, according to an embodiment. In one embodiment, a charging device 136 may be provided having a second charging interface (not shown) configured for electrical connection to the first charging interface 122 of the wearable device 110, to charge the power supply 118.

Figure 7:
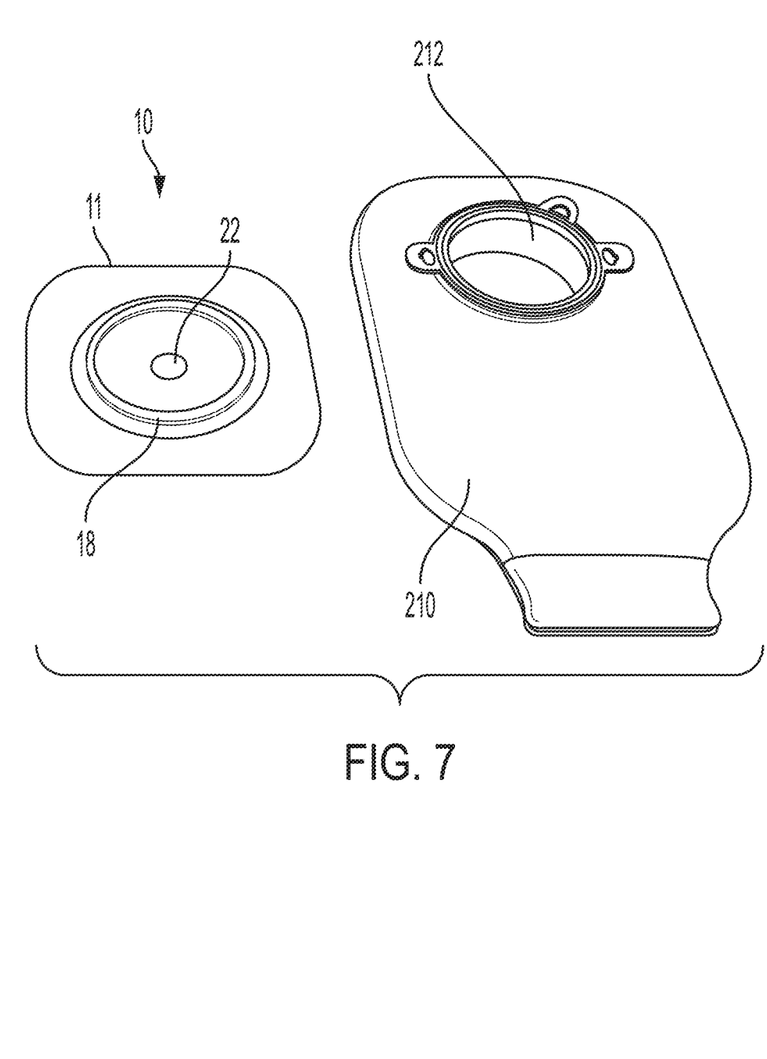
FIG. 7 shows the ostomy hydrocolloid and an ostomy pouch of the ostomy appliance, according to an embodiment.

FIG. 7 shows the ostomy hydrocolloid 11 and an ostomy pouch 210 of the ostomy appliance 10, according to an embodiment. The ostomy pouch 210 includes an inlet opening 212 configured to allow stoma fluid to be received in an internal collection area. The inlet opening 212 may be disposed in fluid communication with the stoma opening 22. In one embodiment, the pouch 210 may include a pouch coupling section 214 configured for coupling to the coupling section 18 of the ostomy hydrocolloid 11.

FIG. 8 schematically shows a personal notification device 310 communicatively connected to the ostomy appliance 10, according to an embodiment. In one embodiment, the personal notification device 310 may be included as a component of the ostomy appliance 10. In one embodiment, the personal notification device 310 may be communicatively connected to the wearable device 110, for example, over a wireless communication interface by way of the wireless transceiver 124.

In one embodiment, the personal notification device 310 may be a mobile communication device, such as a smart phone or other mobile phone. Alternatively, or in addition, the personal notification device 310 may be another mobile communication device, a portable electronic device, or other electronic device configured for communication, directly or indirectly, with the wearable device 110. Such devices may include, but are not limited to, tablets, laptop computers, desktop computers, smart speakers, connected wearable accessories such as fitness trackers, smart watches and the like, smart televisions, personal digital assistants and the like.

In one embodiment, the wearable device 110 may be paired, synced, or otherwise communicatively connected to the personal notification device 310 with a known pairing or syncing operation, which may be initiated, for example, by operation of the operating switch 134.

In one embodiment, the personal notification device 310 may determine the condition of the ostomy appliance 10 and output a notification based on the determined condition, in a manner similar to that described above with respect to the controller 116. In another embodiment, the wearable device 110 may transmit the determined condition of the ostomy appliance 10 to the personal notification device 310.

In one embodiment, the personal notification device 310 may include one or more output devices, such as those described above for example, for outputting a notification based on the determined condition. It is further envisioned that different, or additional, notifications based on the determined condition may be provided on a display screen 312 of the personal notification device 310. For example, graphics, animations and the like may be provided as a notification on the display screen.

In one embodiment, the personal notification device 310 may receive the determined condition, or determine the condition, of the ostomy appliance 10 at predetermined time intervals. Alternatively, or in addition, a user may operate the personal notification device 310 to request the determined condition from the wearable device 110 or to determine the condition.

In one embodiment, the personal notification device 310, embodied as a smartphone, may perform functions according to a smartphone application directed to the ostomy appliance 10. The smartphone application may include program instructions stored in a memory unit of the smartphone which are configured to be executed by a processor of the smartphone to control the smartphone to perform the functions. For example, the smartphone may be controlled to generate and output the notification. The smartphone may also be controlled to store additional data and enable further communications. For example, the smartphone may be configured to track leaks or degradation of the ostomy hydrocolloid 11, behaviors and activities that could potentially affect wear time, including, but not limited to: pouch changes, diet, leakage occurrence, gas occurrence and physical activity.

In one embodiment, the smartphone may be configured to provide a platform to share practices and advice from other users and clinicians. In one embodiment, the smartphone may be configured to allow for communication with other information sources, for example, to access video tutorials providing additional education and instruction on managing a stoma. In one embodiment, the smartphone may be configured to allow for pictures to be taken and stored of the stoma and skin health. In one embodiment the smartphone may be configured to facilitate contact with a wound, ostomy and continence (WOC) nurse (also referred to as an enterostomal therapy (ET) nurse), for example, to troubleshoot or share stoma and skin health conditions. In one embodiment, the smartphone may be configured to allow for ordering or automatic re-ordering of an ostomy appliance 10 or related supplies when a determination is made that such supplies are running low. In one embodiment, the smartphone may be configured to provide usage and patient data to, for example, the ostomy appliance manufacturer, such as marketing, research and product support teams. In one embodiment, such usage and data may be provided, for example, after a user opts-in, and the data may be provided securely, anonymously, and in accordance with local privacy laws and regulations, to support health economics.

Those having ordinary skill in the art will appreciate that the present disclosure is not limited to a smartphone application executed to control functions of a smartphone according to the examples above. For instance, it is also envisioned that a similar software application could be executed by a tablet or other portable device, a remote server configured to be accessed by the user through a known communications interface, or at a personal computing device, such as a laptop or desktop computer, or some combination of the above.

Figure 9A:
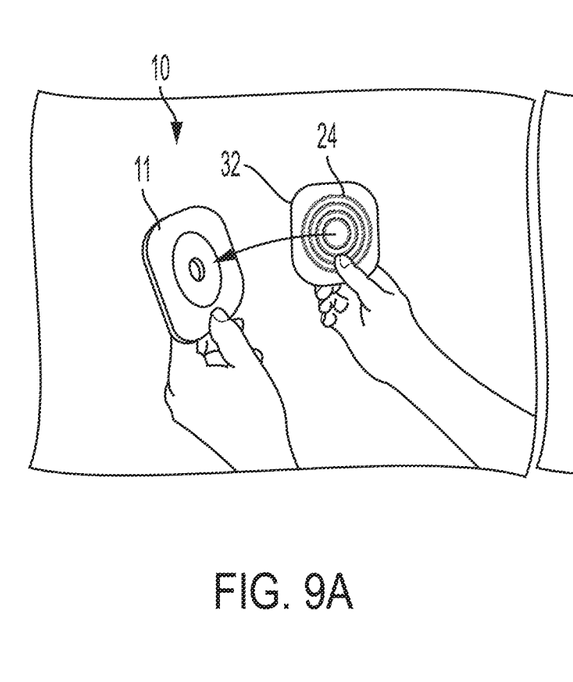
FIGS. 9A-9B show the RFID circuit being applied to the ostomy hydrocolloid, according to an embodiment.
Figure 9B:
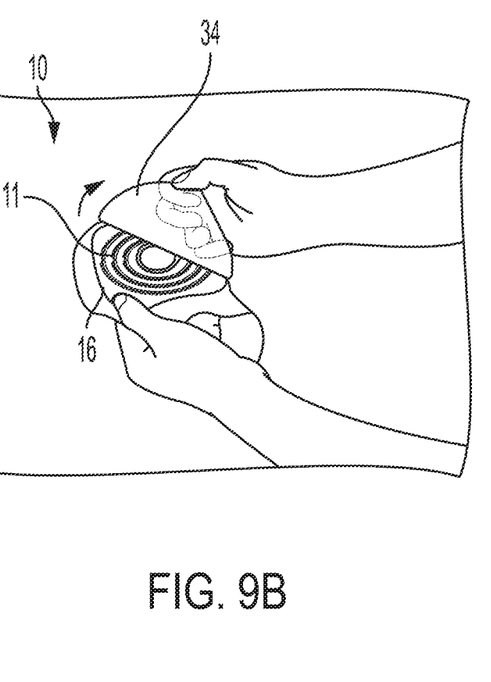

FIGS. 9A and 9B show examples of the RFID circuit 24 being applied to the ostomy hydrocolloid 11. In one embodiment, the RFID circuit 24 may be disposed on the substrate 32 (FIG. 9A). The RFID circuit 24 may be applied to the body-facing side 16 of the ostomy hydrocolloid 11, and a release layer 34 may be removed (FIG. 9B) to expose an adhesive on the RFID circuit 24 for adhering to a user's skin.

Figure 10A:
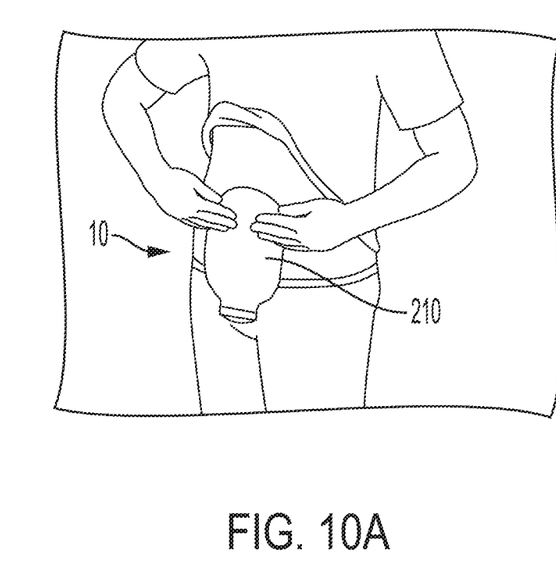
FIGS. 10A-10B show a user setting up the ostomy appliance for use, according to an embodiment.
Figure 10B:
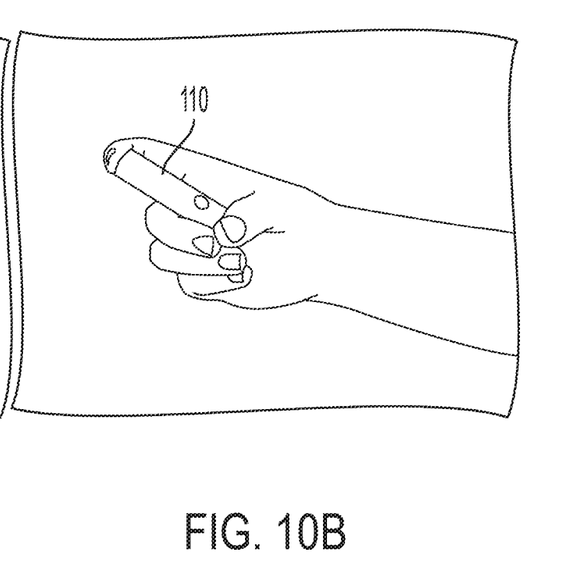

FIGS. 10A and 10B show a user setting up the ostomy appliance 10 for use, according to an embodiment. For example, in FIG. 10A, the ostomy appliance 10, including the ostomy pouch 210, is secured to the user, and in FIG. 10B, the wearable device 110 is powered on and communicatively coupled to the ostomy appliance 10, for example, to the one or more RFID circuit 24.

Figure 11A:
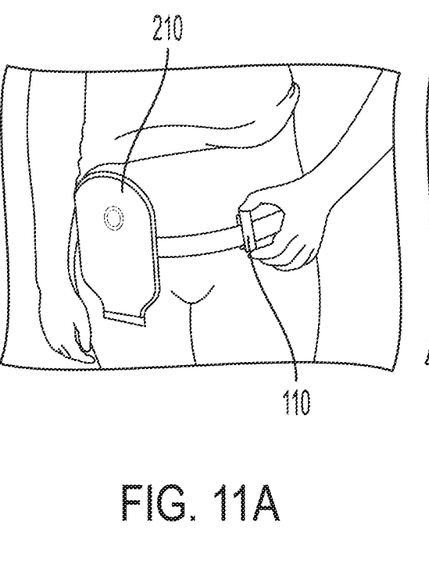
FIGS. 11A-11C show examples the ostomy appliance, in use, configured to detect stoma fluid leakage.
Figure 11B:
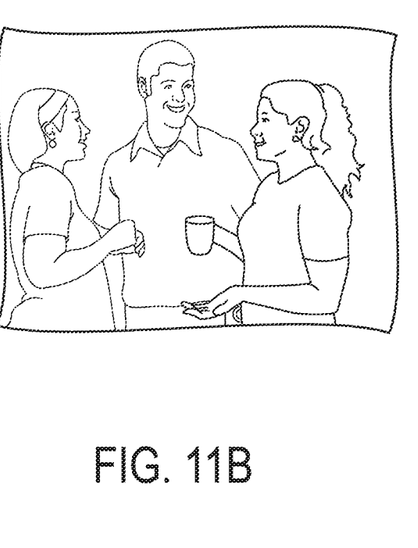
Figure 11C:
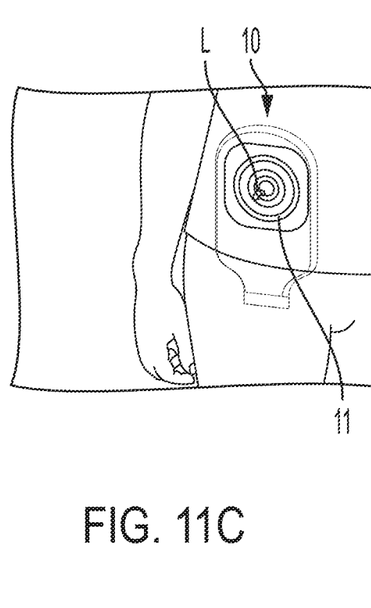

FIGS. 11A-11C show examples the ostomy appliance 10, in use, configured to detect stoma fluid leakage. For example, FIG. 11A shows the ostomy appliance 10, including the ostomy pouch 210 and the wearable device 110 connected to the user. FIG. 11B shows the user in a social setting and FIG. 11C shows ostomy appliance 10 with a stoma fluid leakage 'L' forming along the ostomy hydrocolloid 11.

Figure 12A:
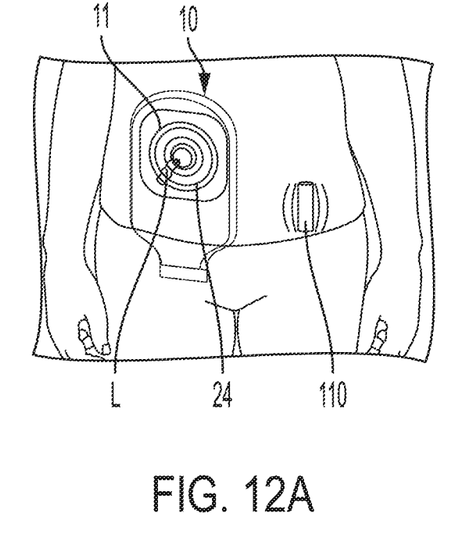
FIGS. 12A-12C show examples of a user tending to the ostomy appliance in response to receiving a notification of stoma fluid leakage.
Figure 12B:
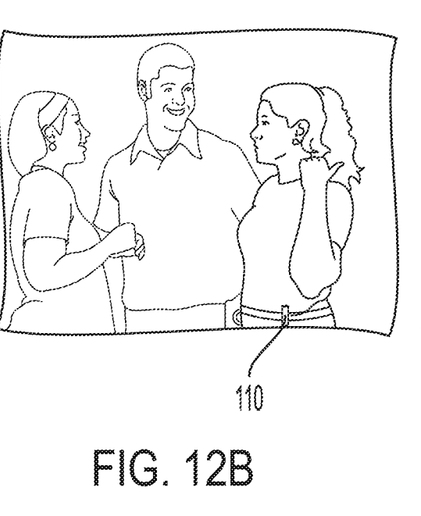
Figure 12C:
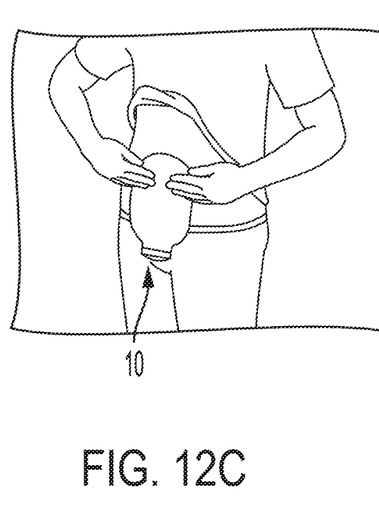

FIGS. 12A-12C show examples of a user tending to the ostomy appliance 10 in response to receiving a notification of stoma fluid leak 'L'. In FIG. 12A, a stoma fluid leak 'L' is detected by a plurality of the RFID circuits 24 and a notification is provided by the wearable device 110. In FIG. 12B, the user discreetly senses the notification. In FIG. 12C, the user tends to the ostomy appliance 10.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:
   a hydrocolloid skin barrier appliance including skin barrier, a backing layer, and a stoma opening extending through the skin barrier and the backing layer; and
   a plurality of Radio Frequency Identification (RFID) circuits disposed on the skin barrier, wherein the plurality of RFID circuits are concentrically positioned relative to one another around the stoma opening, wherein each of the plurality of RFID circuits comprises:
      a RFID transponder having an antenna; and
      a conductive ink connected in series with the antenna and the RFID transponder, wherein the conductive ink is a dissolvable ink configured to dissolve in response to exposure to moisture, wherein the conductive ink is positioned to surround the stoma opening, and wherein the antenna is concentrically positioned to surround the conductive ink, and
   wherein the RFID circuit is in a closed condition when the conductive ink extends continuously between the RFID transponder and the antenna and the RFID circuit is in an open condition when at least a portion of the conductive ink is dissolved.

2. The ostomy appliance of claim 1, wherein the RFID circuits of the plurality of RFID circuits extend along respective substantially circular paths.

3. The ostomy appliance of claim 1, further comprising an ostomy pouch coupled to the hydrocolloid skin barrier appliance.

4. The ostomy appliance of claim 1, further comprising a wearable device communicatively connected to the plurality of RFID circuits, the wearable device comprising:
   a housing;
   a power supply;
   a controller operably connected to the power supply; and
   an RFID transceiver operably connected to a transceiver antenna and the controller.

5. The ostomy appliance of claim 4, wherein the RFID transceiver is configured to transmit a first signal, and wherein the RFID transponder is configured to transmit a second signal in response to receiving the first signal with the RFID circuit in a closed condition and is not configured to transmit the second signal with the RFID circuit in the opened condition.

6. The ostomy appliance of claim 5, wherein the controller is configured to determine a leakage condition of the ostomy appliance based on the second signal.

7. The ostomy appliance of claim 6, wherein the wearable device further comprises an output device configured to output a notification based on the determined leakage condition of the ostomy appliance.

8. The ostomy appliance of claim 4, wherein the wearable device further comprises a wireless transceiver.

9. The ostomy appliance of claim 8, wherein the ostomy appliance further comprises a personal notification device communicatively connected to the wearable device via the wireless transceiver.

10. The ostomy appliance of claim 9, wherein the personal notification device is configured to output a notification based on the determined condition.

11. The ostomy appliance of claim 8, wherein the personal notification device is a smartphone.

* * * * *